(12) United States Patent
Fearnot et al.

(10) Patent No.: US 10,231,703 B2
(45) Date of Patent: Mar. 19, 2019

(54) DEVICES AND METHODS FOR THREE-DIMENSIONAL INTERNAL ULTRASOUND USAGE

(71) Applicant: Muffin Incorporated, West Lafayette, IN (US)

(72) Inventors: Neal E. Fearnot, West Lafayette, IN (US); Peter S. McKinnis, West Lafayette, IN (US); Sarah Robbins, Lafayette, IN (US); Yun Zhou, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 602 days.

(21) Appl. No.: 14/719,367

(22) Filed: May 22, 2015

(65) Prior Publication Data

US 2015/0250451 A1 Sep. 10, 2015

Related U.S. Application Data

(63) Continuation of application No. PCT/US2013/064570, filed on Oct. 11, 2013.

(60) Provisional application No. 61/727,680, filed on Nov. 17, 2012, provisional application No. 61/713,172, filed on Oct. 12, 2012.

(51) Int. Cl.
*A61B 8/00* (2006.01)
*A61B 8/12* (2006.01)
*G01S 15/89* (2006.01)
*B06B 1/06* (2006.01)
*G10K 11/00* (2006.01)
(Continued)

(52) U.S. Cl.
CPC .............. *A61B 8/4466* (2013.01); *A61B 8/12* (2013.01); *A61B 8/445* (2013.01); *A61B 8/4461* (2013.01); *A61B 8/4483* (2013.01); *B06B 1/06* (2013.01); *G01S 15/894* (2013.01); *G01S 15/8943* (2013.01); *G10K 11/004* (2013.01); *G10K 11/352* (2013.01); *A61B 8/0891* (2013.01); *A61B 8/483* (2013.01); *G01S 15/8918* (2013.01)

(58) Field of Classification Search
None
See application file for complete search history.

(56) References Cited

U.S. PATENT DOCUMENTS 4,785,816 A * 11/1988 Dow .................. G01N 29/2487
600/446
4,913,155 A * 4/1990 Dow .................... G10K 11/355
600/446

(Continued)

*Primary Examiner* — Michael J Carey
*Assistant Examiner* — Farouk A Bruce
(74) *Attorney, Agent, or Firm* — Woodard, Emhardt, Henry, Reeves & Wagner, LLP

(57) ABSTRACT

There are disclosed embodiments of devices and methods for ultrasound imaging, for example of the inside of a body part such as a blood vessel. In particular embodiments, a catheter has a tip chamber, within which is an ultrasound transducer mounted on a pivot mechanism, a motor for turning the transducer, and an implement for pivoting the transducer. Examples of such an implement are a second motor operating a shaft or a filament, and the pivot mechanism may be biased to return to a base position when the implement is not pivoting the transducer. In other embodiments, a mirror reflecting ultrasound signals from the transducer may be rotated and/or pivoted, using similar mechanisms.

31 Claims, 9 Drawing Sheets

(51) Int. Cl.
*G10K 11/35* (2006.01)
*A61B 8/08* (2006.01)

(56) References Cited

U.S. PATENT DOCUMENTS

| | | | | |
|---|---|---|---|---|
| 5,740,804 A | * | 4/1998 | Cerofolini | A61B 8/12 600/459 |
| 2003/0073907 A1 | * | 4/2003 | Taylor | A61B 8/12 600/459 |
| 2003/0109786 A1 | * | 6/2003 | Irioka | A61B 8/12 600/459 |
| 2011/0263986 A1 | * | 10/2011 | Park | A61B 8/12 600/462 |

* cited by examiner

DEVICES AND METHODS FOR
THREE-DIMENSIONAL INTERNAL
ULTRASOUND USAGE

The present disclosure concerns devices and methods for ultrasound use within the human body, including devices and methods for employing ultrasound to image the interior of vessels, such as blood vessels. This application is a continuation of PCT/US2013/064570, filed Oct. 11, 2013 which claims the benefit of U.S. Provisional Application Ser. Nos. 61/713,172, filed Oct. 12, 2012 and 61/727,680, filed Nov. 17, 2012, all of which are incorporated by reference in their entireties.

BACKGROUND

Devices have been proposed for using ultrasound imaging within blood vessels to view the condition of the vessel and/or placement or condition of a device placed in the vessel. However, a number of problems with such devices remain. For example, many such devices provide at best an image of a cross section of tissue or other items of interest, i.e. a thin, disk-shaped slice of the interior of a blood vessel with a portion in the center that is not within the range of the ultrasound beam. Current ultrasound imaging thus takes only a view of a two-dimensional cross section. In some other devices, the ultrasound beam is directed at a fixed angle that is not substantially perpendicular to the longitudinal axis (e.g. at 45 degrees). In this case the imaged region is static in the form of a portion of the surface of a cone, also with a center portion that is not within the range of the ultrasound beam. In either case, in order to visualize the entirety of a significant length within the body (e.g. surfaces or portions of tissue, or of devices), the device must be moved along that length, with respective images of cross sections at particular locations taken. Such movement may be inexact, and may include risks associated with blind insertion of the device through the vessel. It is also slow. Typical pull back images take on the order of 30 s to perform (at a speed of about 0.1 mm/s).

Three-dimensional intravascular ultrasound (IVUS) images may be acquired by one-dimensional arrays connected to a mechanical actuator, to move the arrays within the vessel. Such designs are expensive and generally require more space in a device than many vessels will permit. To achieve good image quality, such array transducers must simultaneously transmit and receive on many separate channels. That condition requires many expensive and bulky coaxial cables. Fewer coaxial cables can be used, but doing so reduces the quality of the image and image frame rate.

There remains a need for accurate and efficient application of ultrasound in three dimensions along a substantial length of a vessel or other bodily area, for example to provide a physician with a real-time view along that length. There also remains a need for devices that can view a medical device and one or more tissues or tissue parts simultaneously, particularly in cases in which the device and tissue(s) could not have been imaged reliably in any two-dimensional plane.

SUMMARY

Among other things, there is disclosed apparatus and methods for providing an ultrasound beam with two controllable degrees of freedom within the body of a patient. For example, such apparatus can include a transducer for emitting and/or receiving ultrasound signals, and a rotary motor including a rotatable shaft extending substantially along a rotating axis, wherein operation of the rotary motor rotates the rotatable shaft around the rotating axis. A pivoting mechanism, such as a gimbal mount, is operationally connected to the rotatable shaft of the rotary motor. The pivoting mechanism rotates with the rotatable shaft, and has a base and pivoting member that is pivotable with respect to the base around a pivoting axis, the pivoting axis being substantially perpendicular to the rotating axis. A forcing member is operationally connected to the pivoting member, wherein a force applied to or via the forcing member (which may be a longitudinal force) controls pivoting of the pivoting member around the pivoting axis. In particular examples, the forcing member is a longitudinal member and/or movable with respect to the rotatable shaft. An example of such a forcing member includes a filament such that pulling the filament results in pivoting the pivoting member around the pivoting axis. A gimbal mount apparatus or other pivoting mechanism with control of its angular velocity so that the density of ultrasound scan lines is more uniform is contemplated.

The rotatable shaft may have a longitudinal lumen in some embodiments, and the forcing member can extend at least partially through the lumen. Exemplary forcing members include a longitudinal shaft, e.g. a shaft of a linear motor, the longitudinal shaft extending substantially along the rotating axis, wherein operation of the linear motor moves the longitudinal shaft along the rotating axis. The longitudinal shaft may be operationally connected to the pivoting member to control the pivoting of the pivoting member around the pivoting axis during both turning of the rotatable shaft and operation of the transducer. Particular examples include those where the rotatable shaft of the rotary motor has a lumen therethrough, and the longitudinal shaft of the linear motor has at least a portion extending within the lumen of the rotatable shaft and a distal portion outside of the lumen. The longitudinal shaft may be directly connected to the pivoting member, and/or may have a rounded distal end in contact with the pivoting member. The longitudinal shaft can be connected to the pivoting member by a C-shaped connector, and may be movable in two directions along the rotating axis by the linear motor, wherein movement of the rotating shaft in a first linear direction pivots the pivoting member in a first pivoting direction, and movement of the rotating shaft in a second linear direction pivots the pivoting member in an opposite second pivoting direction. Another type of longitudinal member can include a shape-memory actuator, such as one that contracts when heated to pivot a pivoting member. In these and other examples, a transmission converts linear motion (e.g. of a shaft) to pivoting motion of the pivoting member.

Further examples of such apparatus include those in which the transducer is fixed with respect to or is at least a part of the pivoting member, so that the transducer rotates with the rotatable shaft of the rotary motor, and those in which a mirror fixed with respect to or at least a part of the pivoting member (e.g. a pivoting member which is or includes a mirror) rotates with the rotatable shaft of the rotary motor, and reflects an ultrasonic beam from the transducer. The recited pivoting member is spring-biased in some embodiments to an initial orientation relative to the base, and when force applied to or via the forcing member is released, the pivoting member returns toward the initial orientation.

A tubular member for housing the transducer, rotary motor, gimbal mount or other pivoting mechanism and at least part of the longitudinal member is provided in particular embodiments. Such a tubular member may have a distal chamber defined at least in part by a wall portion of the tubular member, the distal chamber housing at least the transducer and a medium, the wall portion and the medium having similar acoustic impedance to the part of the body into which the tubular member is inserted, so that reflection of ultrasound at the boundary of the medium and the wall portion and at the boundary of the wall portion and body environment is reduced to a level acceptable for imaging through the boundary. The pivotable member optimally has a range of motion around the pivoting axis of a magnitude of at least 150 degrees, particularly for embodiments in which a transducer is connected to the pivoting member. In configurations in which a mirror is or is attached to the pivoting member, for every 1 degree the mirror moves with the pivoting member, the ultrasound beam moves 2 degrees, and so smaller ranges of motion may be adequate. For example, in designs in which placement of the mirror and transducer limits the forward-looking ability of the ultrasound beam (e.g. because the transducer is forward of the mirror and thus in the way of part of the beam) a range of motion about the pivoting axis of about 60 degrees is adequate, since for every 1 degree the mirror moves the ultrasound beam moves 2 degrees, and since some embodiments of mirror designs cannot be forward looking because the transducer is in the way. In some embodiments, e.g. those in which the transducer is fixed with respect to or is at least part of the pivotable member, the pivotable member has a range of motion such that the transducer can be oriented so that it emits ultrasound signals substantially along the rotary motor's axis of rotation and away from the rotary motor.

With the use of two independent mechanical motors, as further described below, the transducer sweep pattern may be set arbitrarily. This allows the transducer to acquire images in flexible ways not possible with existing ultrasound devices. For example, the disclosed transducer system may acquire images in any plane passing through the transducer. Additionally, the transducer may sweep through a three-dimensional region of tissue. The motor platform allows a flexible choice of the sweep pattern. In most dynamic applications where frame rate is important, the image will be restricted to a single plane or small three-dimensional sector. Embodiments in which the rotation of the rotatable shaft about the rotating axis (the rotary motor's axis of rotation) and the pivoting of the pivoting member about the pivoting axis are separably operable at one or more frequencies, so that the user can choose from multiple ultrasound scan patterns. In embodiments in which a rotary motor and linear motor are used, as one illustration, the rotary motor and linear motor are separably operable at one or more frequencies, so that the user can choose from multiple scan patterns. The rotary motor and pivoting mechanism (e.g. via a linear motor) can be configured so that the rotary motor turns faster when the pivoting mechanism is in a state such that the ultrasound signals are pointing in a direction close to the motor's axis of rotation (e.g. more forward-looking), and the rotary motor turns slower when the pivoting mechanism is in a state such that the ultrasound signals are pointing in a direction further from the motor's axis of rotation (e.g. more side-looking). That is, as the signals (or ultrasound beam) move with the pivoting mechanism toward the rotating axis, the angular speed of the signals increases, and as the signals move with the pivoting mechanism away from the rotating axis, the angular speed of the signals decreases.

As discussed in further detail below, the disclosure includes apparatus for ultrasound procedures that includes a transducer for emitting and/or receiving ultrasound signals and first and second motors, wherein the first motor is operatively connected to the transducer so that operation of the first motor turns the transducer around a rotation axis of the apparatus, and wherein the second motor is operatively connected to the transducer so that pivoting motion of the transducer around a pivoting axis transverse to the rotation axis of the apparatus is a function of the operation of the second motor. In particular embodiments, the first motor is a rotary motor and the second motor is one of a linear motor and a rotary motor. The first motor may turn a first shaft having a lumen and operatively connected to the transducer, and the second motor may operate a second shaft that extends through the lumen of the first shaft and is operatively connected to the transducer. Such apparatus can also include a pivoting mechanism operationally connected to the first motor so that the pivoting mechanism rotates in response to operation of the first motor. Exemplary pivoting mechanisms have a base and pivoting member that is pivotable with respect to the base around the pivoting axis, the pivoting axis being substantially perpendicular to the rotation axis. A forcing member may be operationally connected to the pivoting member, wherein a force applied via the forcing member controls pivoting of the pivoting member around the pivoting axis. The transducer can be, or be at least part of, the pivoting member. Particular embodiments of the pivoting mechanism include a pair of arms extending from the base and a sliding plate adapted to slide along the arms and connected to the forcing member, the sliding plate being threadedly connected to the second shaft. The transducer and/or pivoting mechanism is spring-biased in some examples to an initial orientation relative to the base, and when force applied via the forcing member is released, the pivoting member returns toward the initial orientation. The pivoting mechanism may be described in particular instances as a gimbal mount apparatus.

In some embodiments, the second motor is a linear motor, and the forcing member is or includes the second shaft, which extends substantially along the rotation axis. Operation of the second motor moves the second shaft along the rotation axis, with the second shaft being operationally connected to the transducer to control the pivoting of the transducer around the pivoting axis. The second shaft may be directly connected to the pivoting member, or as one alternative the second shaft is connected to the pivoting member by a pivoting connector. The forcing member is movable in some embodiments in two directions along the rotation axis by operation of the second motor, wherein movement of the forcing member in a first linear direction pivots the transducer in a first pivoting direction, and movement of the forcing member in a second linear direction pivots the transducer in an opposite second pivoting direction.

In certain embodiments, the first and second motors are separably operable at one or more speeds, whereby a desired ultrasound scan pattern can be obtained. The first motor can be configured so that the first motor turns faster when the pivoting mechanism is in a state such that the ultrasound signals are pointing in a direction closer to the first motor's axis of rotation, and the first motor turns slower when the pivoting mechanism is in a state such that the ultrasound signals are pointing in a direction further from the first motor's axis of rotation.

Examples of the apparatus, e.g. those for use within the body, can further include a tubular member for housing the transducer and the first and second motors. Such a tubular member can include a distal chamber defined at least in part by a wall portion of the tubular member, the distal chamber housing at least the transducer and a medium. The wall portion and the medium preferably have similar ultrasound passage characteristics to a part of the body into which the tubular member is to be inserted, so that reflection of ultrasound at the boundary of the medium and the wall portion and at the boundary of the wall portion and body environment is reduced to a level acceptable for imaging through the boundary.

In some embodiments, the first and second motors are both rotary motors, and wherein pivoting motion of the transducer is a function of the difference between the rotational speeds of the first and second motors. The forcing member may be one of a flat bar and a formed wire. The arms of the pivoting mechanism may each include at least one limit stop for blocking movement of a sliding plate beyond such limit stops.

A particular example of a pivoting mechanism includes a pair of arms extending from the base, and has an unstressed condition in which the respective angles between each arm and the base are each less than 90 degrees. Each of the arms has a respective indentation and at least one of the pivoting member and the transducer include opposing corresponding indentations. A pair of inserts is provided, each insert placed within respective corresponding indentations of the arms and pivoting member or transducer, so that the pivoting mechanism assumes a stressed condition in which the respective angles between each arm and the base is increased, creating spring force that is sufficient to keep the pivoting mechanism and inserts in place with respect to the arms.

Certain embodiments discussed herein allow images to be acquired in the forward (i.e. generally away from the user) direction. Forward-looking applications open new possibilities for therapeutic guidance. It also allows the placement of the ultrasound catheter with forward visualization, so that the physician can observe with ultrasound the path of the ultrasound catheter and need not place it "blindly." In existing ultrasound catheters, the image plane is behind the distal tip of the device, and so the tip's location in always unobservable via the catheter itself. The ability of the current embodiments to see forward during placement eliminates or reduces hazards of blind placement and/or the need for an external monitor for the ultrasound catheter's progress.

The embodiments disclosed herein are intended to use ultrasound imaging to guide diagnostic or therapeutic medical procedures, including interventions. Examples of such procedures include those in the circulatory system, including IVUS procedures. Three-dimensional capability of the imaging system is considered a major advantage for use in many therapies because of the inherently three-dimensional nature of many procedures. As one example, placement of an abdominal aortic aneurysm graft requires that a guide wire be fed through the contralateral limb of the patient. The location of both the wire tip and the contralateral limb must be known and updated in real time during the placement. Such information cannot be contained in a two-dimensional image or projection, and so use of two-dimensional imaging devices require a "guess and check" method of placement, under external fluoroscopic guidance or two-dimensional ultrasound.

These and other embodiments and examples are discussed in further detail below.

DETAILED DESCRIPTION OF THE ILLUSTRATED EMBODIMENTS

Figure 1:
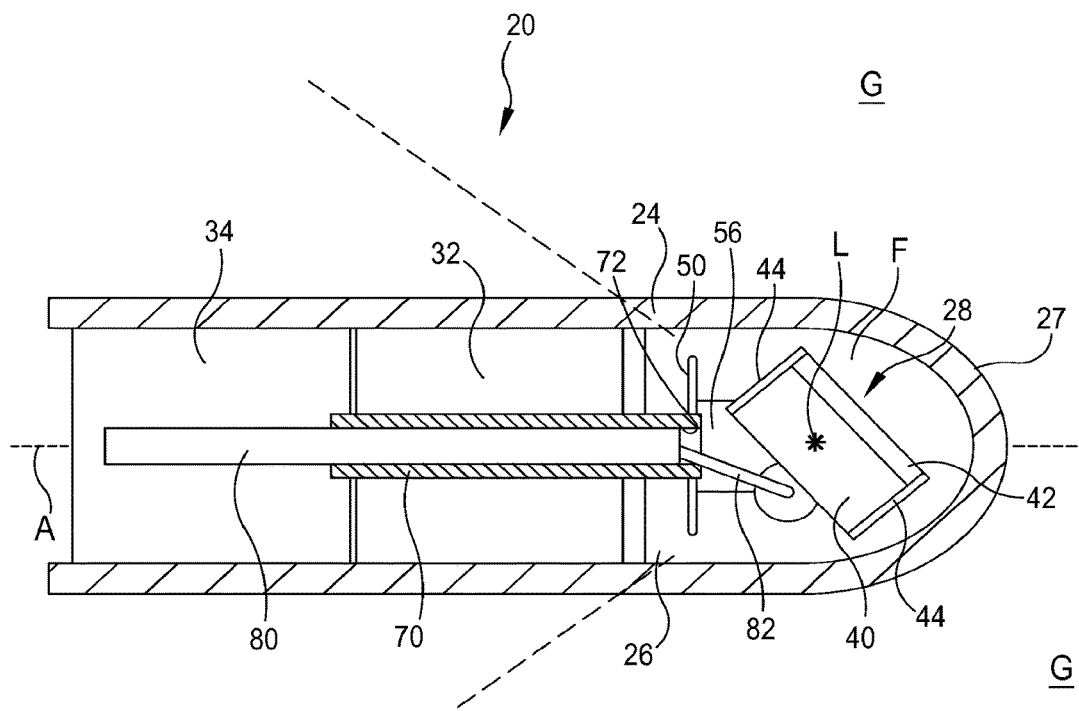
FIG. 1 is a schematic part cross-sectional side view of an embodiment of an end portion of a three-dimensional internal ultrasound device.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated embodiments, and such further applications of the principles of the disclosure as illustrated therein being contemplated as would normally occur to one skilled in the art to which the disclosure relates.

Referring now generally to the drawings, there are shown embodiments of a device 20 for internal ultrasound procedures. Such devices may be diagnostic or therapeutic (including interventional) in application, and include devices inserted percutaneously, subcutaneously or endoluminally into the patient. Examples of such devices include embodiments designed for intravascular ultrasound (IVUS) imaging or treatment.

In the embodiment of FIG. 1, device 20 is a catheter or other flexible elongated or tubular member 22 having a wall 24 defining an internal chamber 26, with catheter 22 being sized and configured for insertion into and/or travel along the vascular system. Within catheter 22 and chamber 26 in this embodiment are a transducer 28, a pivoting mechanism 30 for transducer 28, a rotary motor 32, and a linear motor 34. As will be discussed further below, transducer 28 can be turned around a rotating axis of device 20 as well as pivoted around an axis substantially perpendicular to that rotating axis, allowing the direction of ultrasound emission and reception to extend forward and rearward of the location of transducer 28. In the illustrated embodiments, the rotating axis is the longitudinal axis of device 20, and the pivoting axis is a lateral axis (e.g. perpendicular to the longitudinal axis).

Catheter 22 in the illustrated embodiment is an elongated device of plastic or other sturdy flexible material that presents a barrier to the passage of ultrasound signals small enough (i.e. the difference in acoustic impedance at the boundary of the material and the substances adjacent it) that ultrasound images may be reasonably acquired through the barrier (an "acoustic window"). For example, when used within a blood vessel containing body tissues and blood, it is preferable for catheter 22 to be at least partially (e.g. at least in and/or adjacent to wall 24) constructed of a material which has acoustic impedances similar to that of body fluids such as blood. It will be understood that only the distal end of catheter 22 (e.g. wall 24) need be acoustically transparent, but more or all of catheter 22 may be made of the same material as wall 24 in some embodiments. Possible materials could include, for example, a polymer material such as polyethylene (PE),) polymethylpentene (PMP), or acrylonitrile butadiene styrene (ABS). It has been determined that a preferred thickness of at least the portion of catheter 22 which serves as the viewing window should be approximately ½ of the wavelength corresponding to center frequency.

Figure 1A:
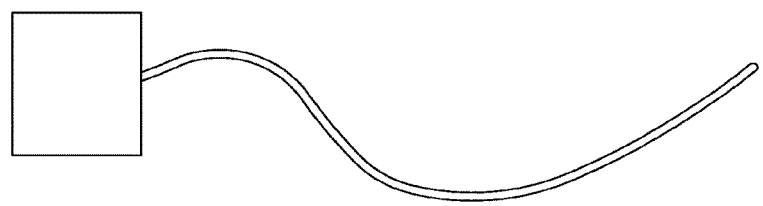
FIG. 1A is a schematic representation of the embodiment of a three-dimensional ultrasound device as in FIG. 1.

Wall 24 surrounds chamber 26, which is at the distal end of device 20 in the illustrated embodiment, and extends proximally. The proximal end of wall 24 and/or catheter 22 may extend outside of the patient during use, and may end in a handle or other operating portion (e.g. an imaging system and/or a maneuvering system schematically indicated at 35 in FIG. 1A). Particular embodiments of catheter 22 or at least chamber 26 are cylindrical, and are sized for insertion into and passage through blood vessels, such as insertion into the femoral artery and passage through it toward the heart. Wall 24 may have a port 27 or other feature to allow injection of fluid into chamber 26 to give chamber 26 ultrasound characteristics similar or substantially identical to that of wall 24 and the surrounding bodily environment (e.g. the blood stream). Sealing members are placed between motor 32 and chamber 26 or the portion of chamber 26 containing transducer 28 and a fluid, in the illustrated embodiments.

Transducer 28 is indicated schematically in the drawings. The term "transducer" should be understood to include an assembly of two or more parts as well as a single piece. It will further be understood that "transducer" as used herein includes devices that transmit ultrasound (i.e. transform an electrical (RF) signal to ultrasound), receive ultrasound (i.e. transform ultrasound to an electrical (RF) signal), or both. If multiple transducers or pieces are provided, transmission of ultrasound may occur at one and reception at another. Transducer(s) as described herein may have one or more piezoelectric elements as respective transducers, and may operate in combination with other transducers within or outside the body. As examples, "transducer" as used herein includes a single element transducer on a rotating and pivoting member, a one-dimensional array of elements on a rotating and pivoting member, and a stationary single element transducer generally aimed at a mirror on a rotating and pivoting member.

An exemplary transducer 28 includes a body or backing layer 40 with a transducer element 42 attached to one side of body 40, and one or more clamping rings 44. An impedance matching layer (not shown) may also be attached to transducer element 42, e.g. opposite body 40. Positioning element 42 as indicated, on the side of body 40, allows both a generally lateral (i.e. away from the rotating axis) and forward ultrasound beam direction depending on pivoting, as further discussed below. Body 40 may substantially absorb ultrasound signals, so that such signals are effectively only projected in one general direction outward from element 42, e.g. to one side or in a limited angular range radially from body 40. Clamping rings 44 have been determined to improve efficiency and mechanical stability of transducer 28. Transducer 28 is capable of sending and receiving ultrasound waves in a range of frequencies which are typically used in medical ultrasound procedures, such as, for example, in the range from 2 MHz to 50 MHz.

Transducer 28 is electronically connected to a power source and to an imaging system. Examples of connections include conductors (e.g. wires or cables) along wall 24, through a central lumen of a motor shaft, via slip ring connections, and/or via metallic film(s) along wall 24. Embodiments of examples are discussed and shown in U.S. Provisional Application No. 61/713,142 (filed Oct. 12, 2012); International Application No. PCT/US2013/064579 (filed on the same date as the present application and entitled "Feedback/Registration Mechanism for Ultrasound Devices"); U.S. Provisional Application No. 61/713,186 (filed Oct. 12, 2012); and International Application No. PCT/US2013/064618 (filed on the same date as the present application and entitled "Mechanical Scanning Ultrasound Transducer with Micromotor"), each of which is incorporated by reference herein in its entirety.

Transducer 28 is mounted in a pivoting mechanism 30 to permit transducer 28 to turn around a rotating axis as well as pivot around a pivoting axis. In the illustrated embodiments, the pivoting mechanism is a two-axis gimbal or gimbal-type mounting, having an outer frame piece or base 50 including a center portion 52 with a hole 54 therethrough and matching arms 56 extending laterally of hole 54 from center portion 52. Hole 54 is sized and configured to accommodate a portion of a shaft from rotary motor 32, so that the shaft can turn pivoting mechanism 30. A pivoting element 58 fits into holes 60 in arms 56. Pivoting element 58 in the illustrated embodiment is a circular disk 62 having side ears 64 that fit into holes 60 and act as an axle, so that element 58 can pivot around the axis defined by ears 64. One or more springs 66 bias pivoting element 58 to a particular initial or original position. In the illustrated embodiment, a torsion spring 66 is connected to an arm 56 at or toward one end, and to an ear 64 at the other (e.g. by inserting an end of spring 66 into a groove in ear 64). A second torsion spring 66 may be similarly attached to the other arm 56 and ear 64, which are not visible in FIG. 2. The particular embodiment shown in FIG. 2 includes a plate 68 fixed to element 58, with plate 68 having a hole 69 for attaching a filament (e.g. suture, string or similar item, not shown). Such a filament can extend from plate 68 through catheter 22 and can be pulled or used to transmit pulling force to plate 68, to pivot element 58.

In particular embodiments, pivoting element 58 may be a backing, base or substrate on which body 40 of transducer 28, or transducer 28 itself, is fixed. In other embodiments, body 40 may include ears so as to become the pivoting element in mounting 30, or a separate axle may be provided with mounting 30 to which body 40 of transducer 28 is directly or indirectly fixed. Mounting 30 permits transducer 28 to turn around a rotating axis, via transmission of rotational motion from rotary motor 32 to mechanism 30, and to pivot transducer 28 at the same time, via pulling or pushing force on body 40 of transducer 28 or a disk portion of pivoting element 58 to move it around the transverse axis formed by pivoting element 58 or a similar axle. Pivoting element 58 is thus able to rotate about both the pivoting and axial directions.

Rotary motor 32 includes a rotating shaft 70 for connecting to mechanism 30, as by interference or similar fit or by other fixed attachment (e.g. by adhesive, solder or welding)

within hole 54 of mounting 30. Rotary motor 32 is a microminiature motor in particular embodiments suitable for containment within chamber 26 of catheter 22. Examples of such microminiature motors include piezoelectric or electromagnetic motors of a size and configuration suitable for containment within chamber 26 of catheter 22 may be used. For example, a particular embodiment of motor 32 is a three-phase, coreless, brushless DC electromagnetic motor, which has few components, small size and minimal complexity. In other examples, a piezoelectric microminiature motor may be used for its advantage of not requiring a gearhead (mechanical transmission) to achieve high torque, and to eliminate problems with torque cables and rotary transformers. A microminiature motor 32 (e.g. electromagnetic or piezoelectric) has a diameter in the range of 0.3 mm to 4 mm in particular embodiments, for example approximately 2.0 mm. Shaft 70 is hollow (i.e. defining a lumen 72 therethrough) in a particular embodiment, and extends through the entirety of motor 32 (e.g. a dual shaft motor). Lumen 72 through shaft 70 permits pulling or pushing mechanisms, electrical conductors, guide wires, or other structures to pass through shaft 70. Pulling or pushing mechanisms, as discussed further herein, operate pivoting element 58.

Rotary motor 32 may be configured to rotate shaft 70 continuously in a single rotational direction. In such embodiments, pivoting mechanism 30 and transducer 28 are rotated around the rotating axis of shaft 70 in that single rotational direction. One or more of the back EMF, the ultrasound signal emitted and/or received by transducer 28, and motor saliency can be used as a feedback mechanism to precisely control the rotational position of rotary motor 32 (and transducer 28 rotated by it) relative to the rest of device 20, ensuring proper registration of images obtained through transducer 28. Registration can be accomplished via methods and structures discussed in U.S. Provisional Application No. 61/713,142 (filed Oct. 12, 2012) and International Application No. PCT/US2013/064579 (filed on the same date as the present application and entitled "Feedback/Registration Mechanism for Ultrasound Devices"), each of which is incorporated herein by reference in its entirety. Rotary motor 32 may alternatively be configured to run in a reciprocating motion, with shaft 70 switching between rotation in a first rotary direction (e.g. for a predetermined time, arc or number of turns) and rotation in a second, opposite, rotary direction (e.g. for a predetermined time, arc or number of turns). Hall sensors (not shown), or ultrasound, back EMF, motor saliency, or a combination of one or more of these, may be used in such a reciprocating embodiment to control and/or monitor angular position of motor 32. Methods and structures relating to a reciprocating motor are discussed in U.S. Provisional Application No. 61/713,135 (filed Oct. 12, 2012) and International Application No. PCT/US2013/064606 (filed on the same date as the present application and entitled "Reciprocating Internal Ultrasound Transducer Assembly"), each of which is incorporated herein by reference in its entirety.

In the illustrated embodiment, linear motor 34 has a shaft 80 that passes through lumen 72 of hollow shaft 70 of rotary motor 32, with a portion of the distal end of shaft 80 extending beyond the end of shaft 70. As indicated above, shaft 80 may be configured to join with shaft 70 so that rotation of shaft 70 also rotates shaft 80, or in other embodiments shaft 80 may remain unrotated by shaft 70 during use, as with a bearing or spacing arrangement (not shown). In either case, shaft 80 is able to move linearly (longitudinally) within and with respect to shaft 70, so that the amount of shaft 80 extending from the end of shaft 70 can vary. As will be discussed further below, the activation of motor 34 may extend and/or retract shaft 80 with respect to shaft 70, so as to use shaft 80 to transmit force to pivoting mechanism 30.

Linear motor 34, in one example, is an electromagnetic motor similar to a voice coil, used extensively for loudspeakers, which operate by creating a high static magnetic flux (e.g. by a permanent magnet) in the lateral direction (e.g. perpendicular to the rotating axis of the motor). An electrically conductive coil is placed through this flux and when current is applied to the coil a force in the axial direction is created, pulling or pushing shaft 80. The placement of the coil, permanent magnet, and magnetic conductors is relatively flexible, and many configurations are possible. Because of angular symmetry, the system can be designed so that shaft 80 can rotate relative to the stator without effecting motor performance. Thus, in some embodiments shaft 80 can rotate with shaft 70 of rotary motor 32 to simplify the system 20, while in other embodiments shaft 80 will remain stationary with respect to the shaft 70 of rotary motor 32.

Shaft 80 is a transmission element, transmitting force generated by linear motor 34 to pivoting element 58 in the illustrated embodiments. As examples, shaft 80 may be a single item that provides forward (pushing) force when linear motor 34 is activated. When motor 34 is deactivated (i.e. forward pushing force is released), then shaft 80 may retract, as by being pushed backward through action of spring 66 on the above-described embodiment of pivoting mechanism 30. In another embodiment (FIG. 3, described further below), single shaft 80 is connected to a C-shaped connector 82, which is also connected to pivoting element 58. In this embodiment, linear motor 34 provides both push and pull control, with activation of linear motor 34 in one mode to push shaft 80 and connector 82, thereby pushing pivoting element 58 and rotating it in one direction around a pivoting axis. Activation of motor 34 in a second mode pulls shaft 80 and connector 82 backward, rotating pivoting element 58 in the opposite direction.

In embodiments in which a bias (e.g. spring 66) is provided, pivoting member 58 (along with transducer 28) and shaft 80 are pushed back by the bias. Where there is no activation or energizing of linear motor 34, shaft 80 and pivoting member 58 will be at an initial static position. In particular embodiments, that initial static position is such that transducer 28 faces substantially laterally (i.e. perpendicularly) to the rotating axis A of device 20, while in other embodiments that initial static position may be such that transducer 28 is turned substantially rearward (i.e. away from the distal end of device 20), e.g. at an angle that would allow some or all of ultrasound signals from transducer 28 to clear motor 32 and/or motor 34. As seen in FIG. 1, a field G of range of the ultrasound beam or signals is indicated by dashed lines oblique to axis A, and encompasses the volume around distal end of device 20, e.g. 270 degrees or more in a given plane. With the bias, motor 34 can be calibrated so that a particular amount of forward force by motor 34, applied against the known bias, will result in a particular amount of travel of shaft 80 and pivoting of pivoting member 58, and therefore a known angle for transducer 28 relative to device 20 and the vessel in which it is placed.

Figure 3:
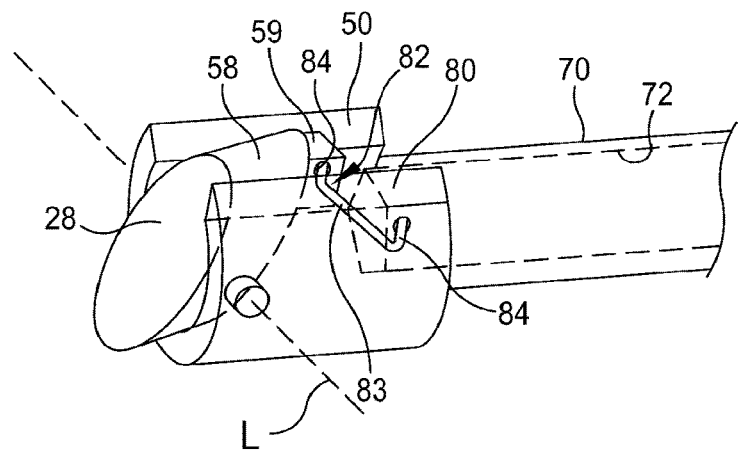
FIG. 3 is a perspective view of another embodiment of a pivoting mechanism useful in the embodiment of FIG. 1.

An example of a push-pull mechanism connecting shaft 80 with pivoting member 58 is shown in FIG. 3. A C-shaped connector 82 has a middle portion 83 and two end portions 84 that are substantially perpendicular to middle portion 83 in this embodiment. One end portion 84 is attached to pivoting member 58, as through insertion into a hole in pivoting member 58, which may be in an extension on member 58 as exemplified in FIG. 3. The other end portion 84 is attached to shaft 80 in much the same way, as by inserting it into a hole in shaft 80. End portions 84 are pivotable with respect to their respective connected parts (pivoting member 58 or shaft 80 in particular embodiments). Forward motion (to the left in FIG. 3) of shaft 80 pushes connector 82, with one end portion 84 pushing on pivoting member 58 to pivot it around pivoting axis L. In the illustrated embodiment, such pushing causes a counterclockwise rotation of pivoting member 58 around axis L, as viewed in FIG. 3. Retraction of shaft 80 via reversal of linear motor 34 pulls connector 82, with an end portion 84 pulling pivoting member 58 to pivot it clockwise (as viewed in FIG. 3) around pivoting axis L. Control of the position of shaft 80 thus controls the angular position of pivoting member 58 and transducer 28.

Figure 2:
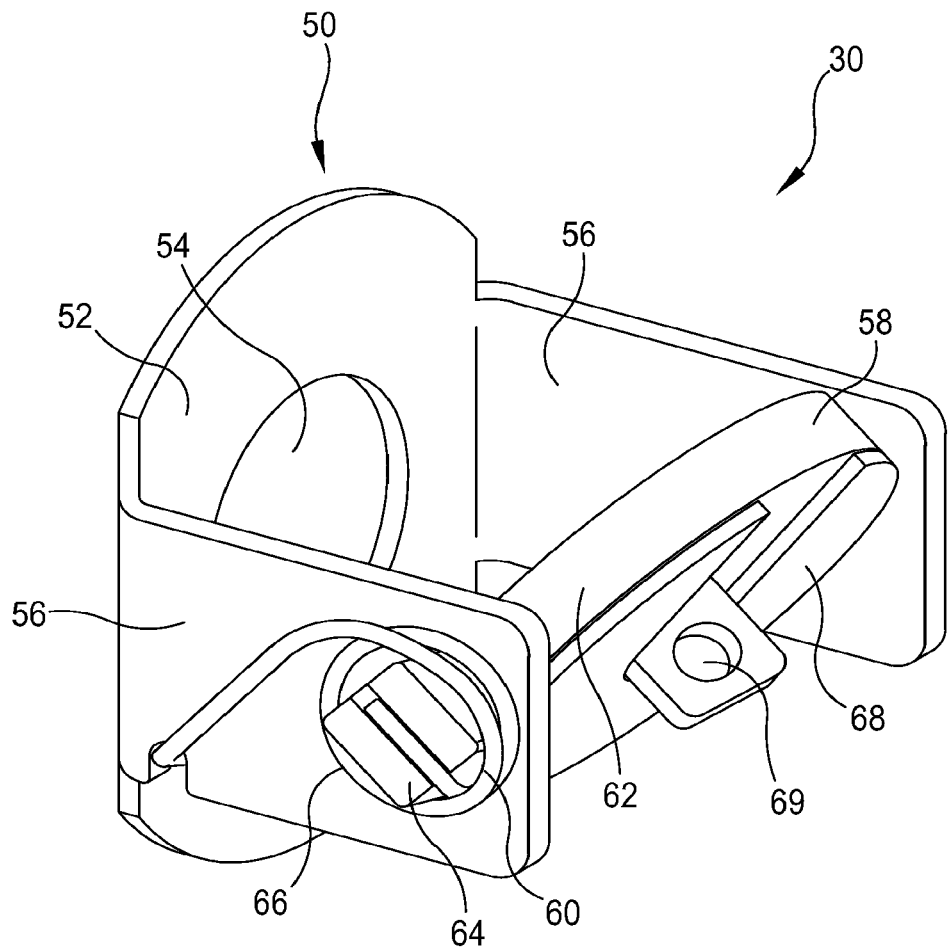
FIG. 2 is a perspective view of an embodiment of a pivoting mechanism useful in the embodiment of FIG. 1.

The embodiment of a pivoting mechanism 30 shown in FIG. 3 has many similarities to FIG. 2, and shows a substantially U-shaped pivoting frame or base 50 within which is pivotably fitted a pivoting member 58. Pivoting member 58 is fitted so as to be pivotable within frame 50 around pivoting axis L. In this embodiment, transducer 28 is at least part of the pivoting member, and conductors to transducer 28 are not shown for clarity in the drawing. Pivoting member 58 in this embodiment includes an extension 59 with a hole for connector 82. As seen in FIG. 3, in this embodiment extension 59 is at or adjacent the perimeter of pivoting member 58. Shaft 70 of rotary motor 32 and shaft 80 of linear motor 34 are shown.

Figure 4:
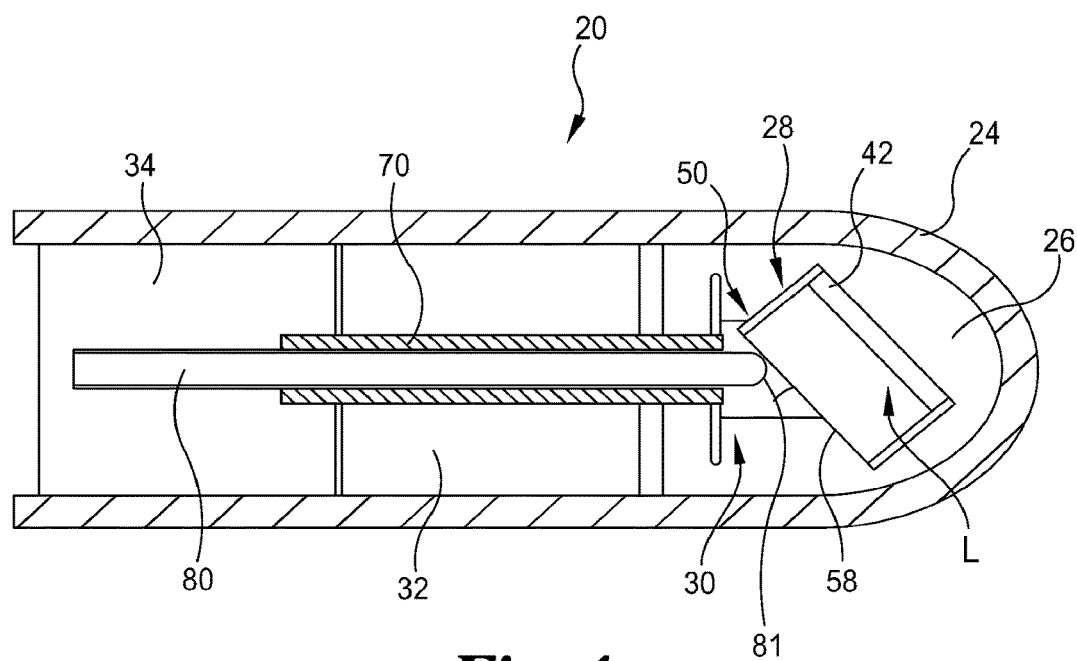
FIG. 4 is a schematic part cross-sectional side view of an embodiment similar to that of FIG. 1 with a particular embodiment of internal structure.

In the embodiment of FIG. 4, shaft 80 has a rounded tip portion 81 that is adapted to engage pivoting member 58 on a side opposite to transducer 28 or transducer element 42. Pivoting member 58 and transducer 28 are connected to a base or frame 50 so that they can pivot about pivoting axis L. As shaft 80 is moved forward (rightward, as seen in FIG. 4), it pushes pivoting member 58 at a point offset from the pivoting axis L. Pivoting member 58 rotates around the pivoting axis L (clockwise as seen in FIG. 4) against the bias of pivoting member 58 (e.g. from spring 66 seen in FIG. 2). When pushing force is partially or entirely released, the bias returns pivoting member toward or to an initial position, pushing shaft 80 proximally. Rounded tip portion 81 is advantageous as it permits the application of the pushing force while pivoting member 58 of a pivoting mechanism 30 is turning around the rotating axis, and presents a small surface (e.g. a tangent point) against pivoting member 58, reducing friction between tip portion 81 and pivoting member 58. In embodiments in which no spring or similar bias is provided for mounting element 30, a feedback sensor (not shown) can be operatively connected to shaft 80 to determine how far shaft 80 is extended from shaft 70, and thereby how much pivoting of pivoting member 58 has taken place. A return force or bias can be provided by centripetal force.

Device 20 provides an ultrasound signal sweep or field that not only turns around the rotating axis A of device 20 but also is pivotable to look forward and/or rearward of the particular position of transducer 28. For example, a pivoting element (e.g. element 58 with transducer 28) is able to rotate about both pivoting and rotating axes. In embodiments having linear motor 34, shaft 80 is operatively connected to mounting element 30.

Other embodiments for controlling the pivoting of transducer 28 are also contemplated. For example, a length of flexible material 90, such as a cord, string, suture or similar filament, can be placed along device 20, through hollow shaft 70 of rotary motor 32 to plate 68 of pivoting element 58. Pulling cord 90 transmits tension to pivoting element 58, resulting in pivoting in a clockwise direction (as seen in the example of FIG. 2) against the bias of torsion spring 66. When pulling on cord 90 ceases, the bias of spring 66 returns pivoting element 58 (and transducer 28) to an original static position. Such a cord 90 may be attached to linear motor 34 and/or shaft 80, so that linear motor 34 provides pulling force.

As another example, a push-only linear force may be provided, against a bias provided in an opposing direction to the bias indicated above by torsion spring 66. A rigid shaft 102 is attached to linear motor 34, and activation of linear motor 34 forces shaft 102 forward, in turn pushing the side of pivoting element 58 and causing rotation of pivoting element 58.

In other embodiments of device 20 in which motion around one axis (a pivoting or rotational axis) of transducer 28 is preferred to be slower, a shape memory actuator (SMA) can be employed. For instance, where a slower pivoting axis is desired, the SMA may be used as a forcer in place of shaft 80 and linear motor 34. The SMA uses a material that changes shape as one or more operating characteristics changes. A typical example is a wire of nickel-titanium alloy configured to contract when heated due to the material's shape memory properties, with the contraction being about 3% of the total length of the wire. The wire may be heated by current passing through it, and when such current is removed, the wire cools and expands toward its original length. Bias force may be provided to assist the expansion.

Figure 6:
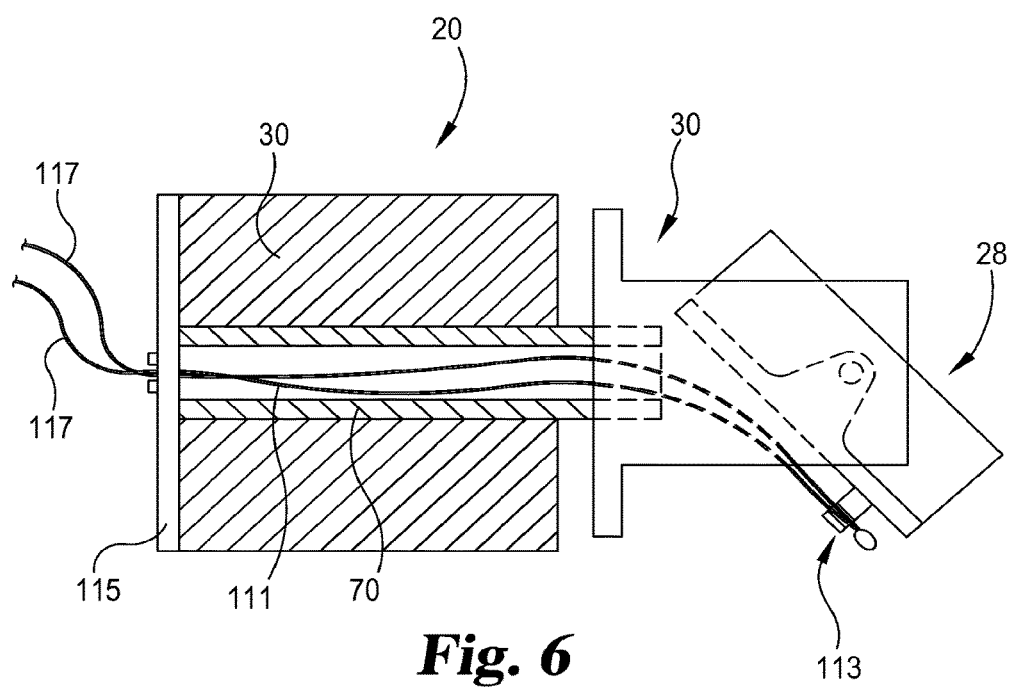
FIG. 6 is a schematic part cross-sectional side view of an embodiment similar to that of FIG. 1, showing shape-memory actuator.
Figure 7:
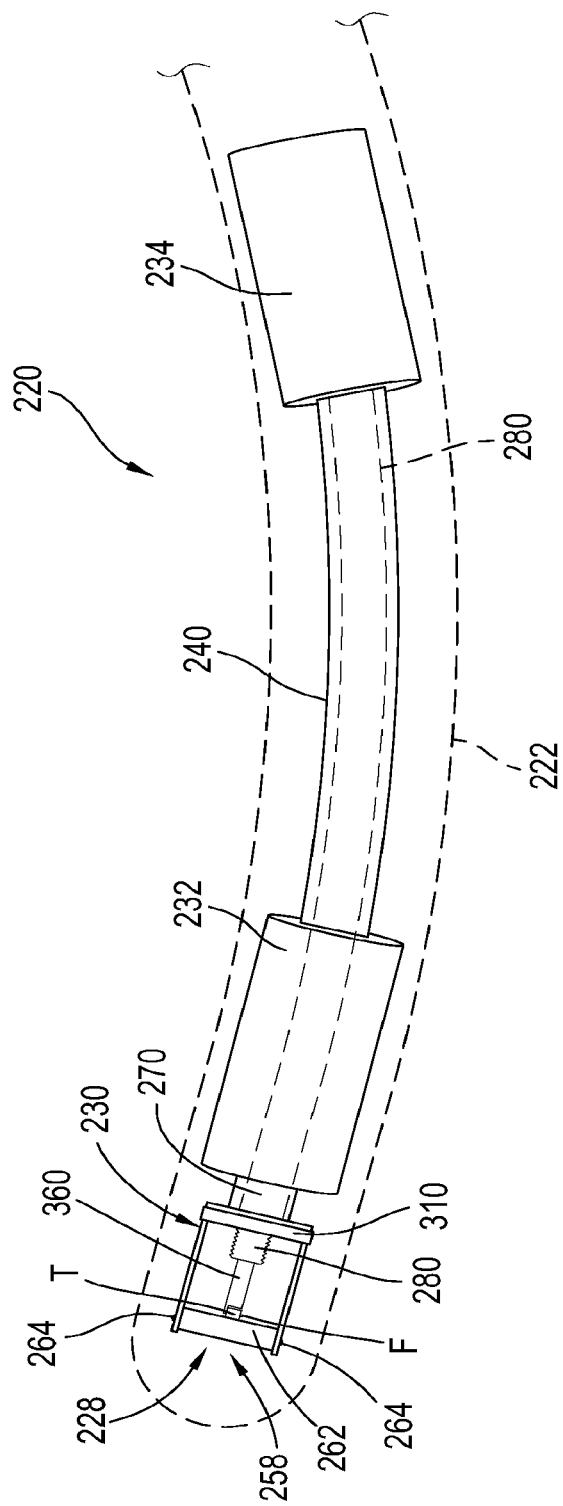
FIG. 7 is a side view of an embodiment of a three-dimensional ultrasound device.
Figure 8A:
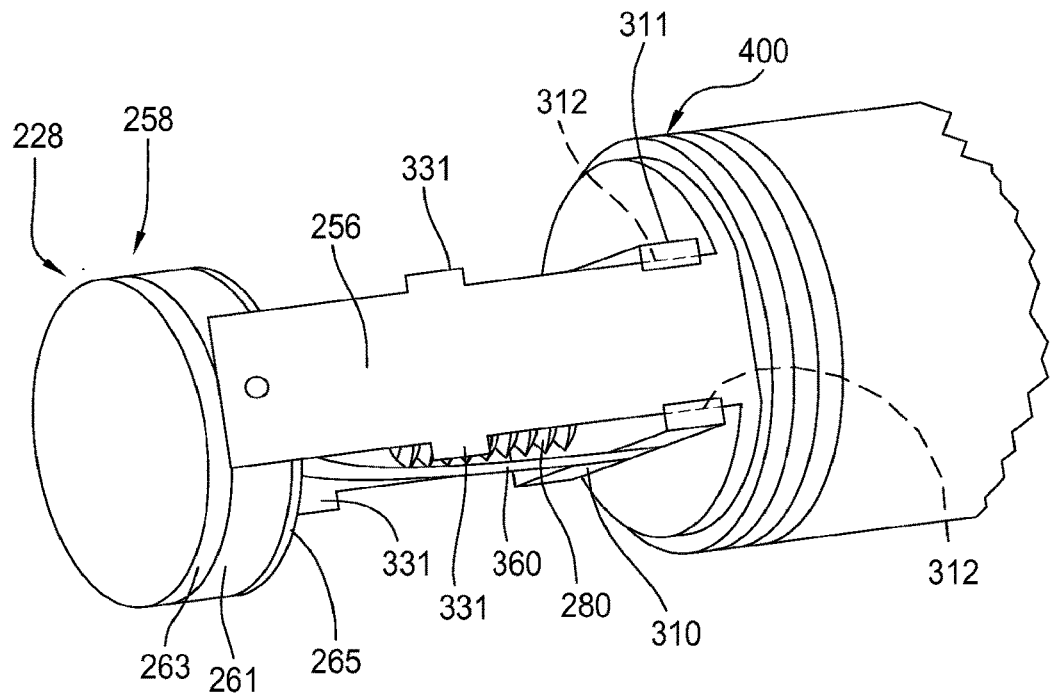
FIG. 8A is a perspective view of a portion of the embodiment of FIG. 7 in a first condition.
Figure 8B:
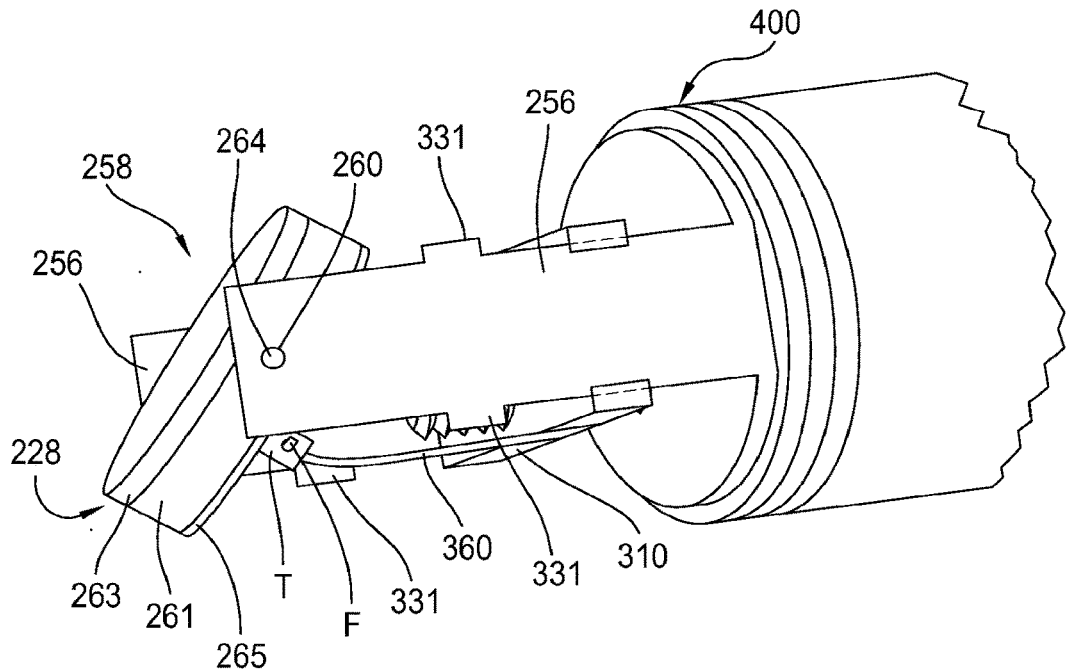
FIG. 8B is a perspective view of a portion of the embodiment of FIG. 7 in a second condition.
Figure 8C:
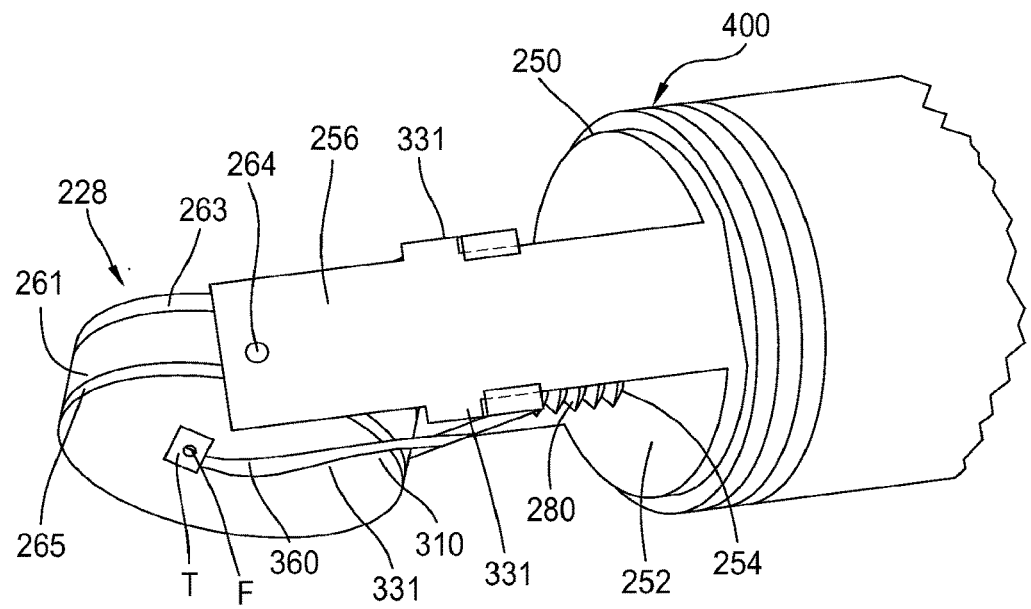
FIG. 8C is a perspective view of a portion of the embodiment of FIG. 7 in a third condition.

In FIG. 6, there is shown an embodiment of device 20 in which a wire 111 of one or more filaments of SMA material, e.g. nickel-titanium wire as noted above, fits through lumen 72 in shaft 70 of rotary motor 32 to link to a pivoting mechanism 30, as at a slip tension joint 113. Slip tension joint 113 allows transducer 28 to rotate, while wire 111 does not rotate. Wire 111 is connected to a rigid plate 115 that constrains linear motion of wire 111, which in this embodiment is fixed to motor 32. Wire 111 is further connected to a source of electrical current, as by one or more wires 117. When the current is applied, wire 111 warms (e.g. a cycle on the order of 0.1 seconds for small diameter wire), and as it warms, it changes shape by contracting in length generally along the rotating axis within shaft 70, causing the inclination of wire 111 to decrease (i.e. point more toward the rotating (longitudinal) axis of device 20. The contraction and/or inclination change by wire 111 pulls on a portion of pivoting mechanism 30 (e.g. slip tension joint 113), pivoting the pivoting mechanism around the pivoting axis, substantially as described above when shaft 80 moves along the rotating axis. Discontinuing the current allows wire 111 to cool and extend toward its prior length, and as described above, such a change can be turned into pivoting of transducer 28 back to an original position or orientation, as by a bias.

Figure 5:
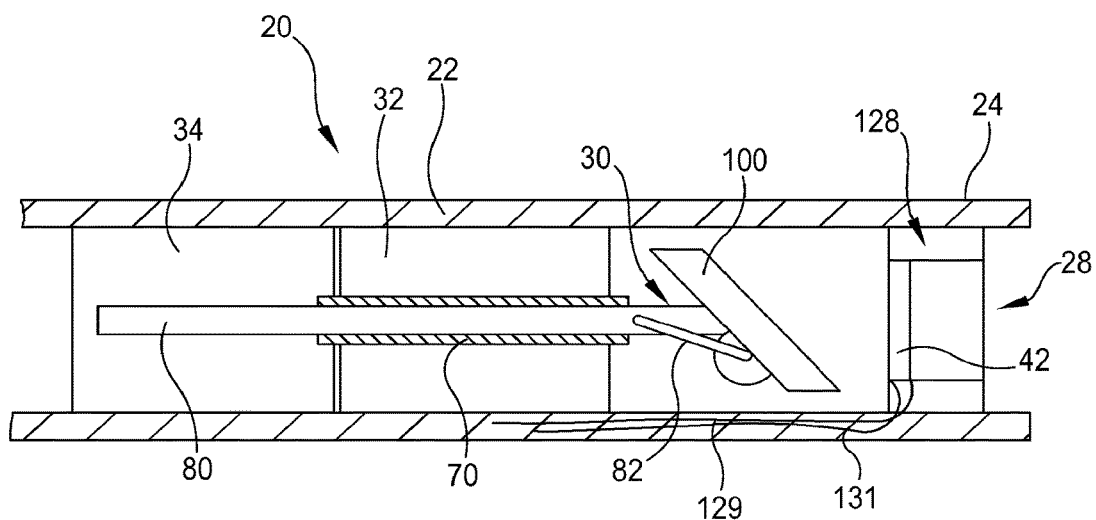
FIG. 5 is a schematic part cross-sectional side view of an embodiment similar to that of FIG. 1, showing a pivotable mirror and a stationary transducer.

Embodiments noted above have placed transducer 28 in contact or association with pivoting element 58, so that turning mounting member 30 via rotary motor 32 and adjusting pivoting element 58 via linear motor 34 acts essentially directly on transducer 28. In these embodiments, transducer 28 is turned and pivoted to emit and receive ultrasound signals directly to the vessel or other tissue. It will be understood that other embodiments of device 20 (e.g. FIG. 5) can include a mirror 100 attached to or associated with pivoting mechanism 30 (e.g. particularly pivoting member 58), so that mirror 100 turns through the action of rotary motor 32 and pivots through the action of linear motor 34. A stationary transducer 128 (at the distal end of device 20 in this embodiment) emits ultrasound signals which reflect from mirror 100 to the tissue, and mirror 100 reflects the returning signal to transducer 128. Conductors 129, 131 are provided to transfer electrical signals to transducer 128 for creation of ultrasound waves, and to transfer signals representing ultrasound echoes from transducer 28 to an imaging system. The ultrasound beam from and to transducer 128 moves two degrees for every one degree of pivoting by mirror 100, in such embodiments, and thus such embodiments provide a similar or wider field for the ultrasound beam as is provided above, with a smaller or similar linear motion or force provided by linear motor 34.

To address ultrasound reflectivity at the boundary between chamber 26 and blood or other body fluid in which device 20 is placed, a fluid F is placed in chamber 26 that presents ultrasound-carrying characteristics that are similar to the fluid outside of chamber 26. In embodiments used for IVUS procedures, examples of fluid F can be a saline solution, mineral oil, castor oil or other types of oils, or alcohols, so that the ultrasound characteristics (e.g. acoustic impedance) within chamber 26 are similar to those outside chamber 26 (i.e., blood in a blood vessel). A port P may be placed in the wall 24 bounding chamber 26 to allow a user to inject fluid F into chamber 26 just prior to use of device 20. Port P can then self-seal, so that little or no fluid F escapes from chamber 26. One or more seals may be placed in device 20 to separate fluid F in chamber 26 from motor(s) 32, 34. Saline and/or alcohol have very good acoustic transmission and low viscosity (low friction), but they are corrosive and must be injected or otherwise placed in chamber 26 at the time of use. Oils (e.g. mineral or caster oil) have slightly worse acoustic properties and much higher viscosity (higher friction), but may be placed in chamber 26 well before using device 20.

An example of using device 20 in the context of IVUS will now be given. As previously noted, it will be understood that devices as disclosed herein may be used in other types of internal procedures as well.

Device 20 is prepared (e.g. by injecting fluid F into chamber 26, if not already present) and inserted into a blood vessel of a patient and maneuvered to a desired location within the vasculature. Transducer 28 may be operated during travel to the desired location, since the transducer 28 can be pivoted through use of linear motor 34 or other linear force-provider to face at least generally forward of device 20. Throughout placement and at a desired imaging location, rotary motor 32 can be operated to turn transducer around the rotating axis to provide images around device 20, and linear motor 34 (as one example) can be operated to pivot transducer around a pivoting axis to shift the ultrasound field forward and/or backward. Controls for motors 32 and/or 34 (not shown) may be provided to maintain one or both at a particular rotational speed or pattern. For example, modalities such as a spin around the rotating axis of between 30-100 Hz may be combined with a slower pivoting around the pivoting axis of about 1-2 Hz, to provide clear images forward and backward in a defined pattern. It has also been determined that a relatively slow spin around the rotating axis (e.g. about 1-2 Hz) combined with pivoting around the pivoting axis more rapidly, e.g. near a resonant frequency of device 20 can provide good results. A modality providing a faster rotation around the rotating axis when transducer 28 is pointed closer to the rotating axis and slower rotation around the rotating axis when transducer 28 is further from the rotating axis is also useful for improving the image frame rate and clarity. Imaging continues, with adjustments to the positioning of transducer 28 and the ultrasound field, as the physician deems necessary or useful.

Embodiments of device 20 used in IVUS would preferably be about 2.7-3.0 mm or less in diameter, so as to be effective in the human vasculature. Linear motor 34 and rotary motor 32 each may have a length of approximately 2.5 mm in particular embodiments. With mounting 30 and transducer (piezoelectric element) 28 included, an overall length may be approximately 10 mm in overall length. While device 20 is described in part above in the context of intravascular (IVUS) uses, it will be understood that embodiments of device 20 could also be used for other medical procedures and/or with a variety of other medical devices. The versatility of the embodiments described herein allows IVUS to be used to guide percutaneous therapeutic interventions such as for example embolism coils, stents, filters, graphs, balloons, biopsies, and administering therapeutics, etc. Device 20 can be used to locate various anatomical landmarks that will be used to correctly place or guided therapy. Typical landmarks include confluences, bifurcations, side branches, nearby vessels, nearby nerves, the heart, and other tissues adjacent to vessels or other orifices containing the IVUS transducer. Device 20 can also be used to locate diseased tissue that will be treated or avoided. Device 20 can be used during a biopsy to provide an image of a needle being deployed into tissue. During a TIPS procedure an image can be produced to allow a physician to watch a needle being placed into the portal vein. For AAA delivery, device 20 can allow a physician to place a guide wire into a contralateral leg. Device 20 could also be used to image the location of a deployed implantable device both during and after deployment.

FIGS. 7-10 represent embodiments of structure of a device 220 for internal ultrasound procedures. This embodiment of device 220 includes a transducer 228, pivoting mechanism 230, device side rotary motor 232, a control side rotary motor 234, and a motor linkage 240 between motors 232 and 234. The numbers used with respect to this embodiment parallel those used in prior embodiments, with the addition of the prefix 2. The features of device 220 are intended in particular embodiments to be housed within a catheter 222, essentially as described above with respect to device 20 and catheter 22.

Device side rotary motor 232 is the motor located closer to the application end of device 220, nearer pivoting mechanism 230. Motor 232 is a microminiature motor in particular embodiments suitable for containment within catheter 222, such as an electromagnetic motor or piezoelectric motor, specific examples of which are discussed above with respect to motor 32. Motor 232 includes a hollow rotating shaft 270 for connecting to mechanism 230 in this embodiment, in which operation of motor 232 turns shaft 270. It will be understood that operation of motor 232 and shaft 270 may include steps or features indicated above with respect to operation of motor 32 and shaft 70. The rate of rotation of device side rotary motor 232 determines the rate of rotation of shaft 270 and mechanism 230. The lumen through shaft 270 permits pulling or pushing mechanisms, electrical conductors, wire guides or other structures to pass through shaft 270. As discussed below, in this embodiment particular structure for effecting the pivoting of transducer 228 passes through the lumen of shaft 270.

Control side rotary motor 234 is located closer to the application end of catheter 222 of device 220. Like device side rotary motor 232, control side rotary motor 234 is a microminiature motor (e.g. an electromagnetic or piezoelectric motor) that produces rotational motion in threaded shaft 280. Shaft 280 is a part of or connected to motor 232, and passes through hollow shaft 270 of device side rotary motor 232, with a portion of the distal end of shaft 280 extending beyond the end of shaft 270. In the illustrated embodiment, shaft 280 is threaded over its entire length, while in other embodiments shaft 280 may be threaded only over one or more discrete portions, e.g. a portion that passes through hollow shaft 270 and extends beyond hollow shaft 270. Shaft 280 is able to turn within and with respect to shaft 270. The rate of rotation of control side rotary motor 234 controls the rate of rotation of threaded shaft 280. As will be discussed further below, the relative rates of rotation of motors 232 and 234 provide pivoting action for transducer 228.

Motor linkage 240 connects control side rotary motor 234 to device side rotary motor 232 in the illustrated embodiment. Linkage 240 is shown as a tube through which threaded shaft 280 extends, keeping threaded shaft 280 from contacting the wall of catheter 222. In some embodiments, the connection of linkage 240 to each motor 232, 234 provides bracing between the motors, limiting or eliminating any tendency for motors 232, 234 to move toward or away from each other. Linkage 240 is made of a material that is laterally flexible in preferred embodiments to allow it (with device 220) to bend as it is passed through a vessel. A configuration in which motors 232 and 234 are abutting or closely adjacent is contemplated, with linkage 240 eliminated or substantially reduced, although such a configuration may limit the amount of flexibility and bending in the region of the motors.

Transducer 228 in one embodiment is substantially as described above with respect to transducer 28. Transducer 228 is mounted in pivoting mechanism 230 to permit transducer 228 to turn around a rotating axis as well as pivot around a pivoting axis. The illustrated embodiment of mechanism 230 is a gimbal-type mounting similar to mechanism 30 discussed above, having an outer frame piece or base 250 including a center portion 252 with a hole 254 therethrough and matching arms 256 extending laterally of hole 254 from center portion 252. Center portion 252 is fixed to or with respect to shaft 270 of motor 232, so that shaft 270 can turn pivoting mechanism 230. Hole 254 is sized and configured to threadedly accommodate a portion of shaft 280 from motor 234. A pivoting element 258 fits into holes 260 in arms 256 in the embodiment of FIGS. 7-8. Pivoting element 258 in the illustrated embodiment is a circular disk 262 having side ears or pivot points 264 that fit into holes 260 and act as an axle, so that element 258 can pivot around the axis defined by ears 264. In particular embodiments, pivoting element 258 may be a backing, base or substrate on which all or a part of transducer 228 is fixed, or may be a portion of transducer 228, as in the discussion of element 58 and transducer 28 above.

Mechanism 230 in this embodiment includes a sliding member or plate 310 in contact with arms 256. Sliding member or plate 310 has respective lateral sides 311 in this embodiment each having top and bottom grooves 312. Arms 256 of mechanism 230 are within grooves 312 of plate 310, so that plate 310 can slide along the arms, moving linearly with respect to mechanism 230. Member 310 includes an opening 313 therethrough, which in the illustrated embodiment is substantially in the center of member 310. Plate 310 may be thin so that the rim or edge of opening 313 acts as a thread that is compatible with the thread of shaft 280, or the rim or edge of opening 313 may be internally threaded so as to engage the threads of threaded shaft 280.

In the illustrated embodiment, the range of movement of plate 310 along arms 256 is defined by limit stops 331 on the arms of the pivoting mechanism 230. Limit stops 331 are shown in this embodiment as raised portions or bosses extending from the arms, e.g. a square or rectangular tab in the plane of and monolithic with the arm 256. The sites of limit stops 331 determine the maximum amount of movement of plate 310 by creating a location relative to arms 256 at which plate 310 is blocked from further sliding along arms 256. In particular embodiments, limit stops 331 are placed only at a location distal of center portion 252, so that plate 310 can slide at most between center portion 252 (acting as a control-side limit stop) and limit stops 331, while in other embodiments a set of limit stop(s) 331 may be placed inside center portion 252 and another set of limit stop(s) 331 further distally. Part or all of plate 310 and/or of arms 256 can be made from or coated with a low friction material (e.g. PTFE (Teflon)) to make the sliding of plate 310 over arms 256 easier.

Because plate 310 is connected to arms 256, it rotates along with pivoting mechanism 230 at a rate of speed that is determined by the rotation of shaft 270 by device side rotary motor 232. Plate 310 is also threadedly connected to threaded shaft 280, as threads of shaft 280 engage plate 310 through opening 313. The rate of rotation of threaded shaft 280 is determined by control side rotary motor 234. When the rates of rotation of shafts 270 and 280 are the same, i.e. the relative rotational speed of the shafts is zero, then there is no relative rotation between plate 310 and shaft 280, and so threaded shaft 280 does not force plate 310 in either direction along arms 256. When there is a non-zero relative rotational speed between shafts 270 and 280, then there is a relative rotation between shaft 280 and plate 310, and the threaded engagement between shaft 280 and plate 310 results in longitudinal movement of plate 310 along shaft 280 and arms 256.

A forcing member 360 (akin to shaft 102 described above) is attached to plate 310, and in the illustrated embodiment member 360 is connected to pivoting element 258 on one end and to the side of the pivoting axis. As an example, pivoting element 258 can include a tab T that extends from pivoting element 258 opposite (e.g. substantially perpendicular) from transducer 228. Forcing member 360 can include a distal finger F that connects to tab T, as by extending through a hole or slot in tab T (e.g. FIGS. 7, 8A-8B), so that member 360 can pivot with respect to tab T. With forcing member 360 attached to plate 310 and connected to pivoting element 258, movement of plate 310 causes the forcing member 360 to apply force to pivoting member 258, which rotates pivoting member 258 (with transducer 228) around the axis defined by ears 264.

Forcing member 360 in the illustrated embodiment is a flattened bar that preferably has little or no longitudinal elasticity, so that movement of plate 310 is efficiently transmitted to pivoting element 258. Forcing member 360 may have some bendability about an axis perpendicular to the longitudinal axis, as suggested in the drawings, particularly as plate 310 and pivoting member 258 approach their respective limits of movement. A suitable forcing member may be of other shapes or materials that provide for transmission of enough force to pivot member 258 when sliding plate 310 moves along arms 256, such as a C-shaped wire structure or similar member described above.

Mechanism 230 permits transducer 228 to turn around a rotating (e.g. longitudinal) axis, via transmission of rotational motion from motor 232 to mechanism 230 via shaft 270. Mechanism 230 permits pivoting of transducer 228 around a pivoting axis (e.g. perpendicular to the rotating axis) at the same time, via pulling or pushing force on pivoting element 258 transmitted via member 360 from sliding plate 310. Plate 310 is moved along arms 256 when the rotational speed of threaded shaft 280 is different from the rotational speed of shaft 270, so that a non-zero rotational speed of shaft 280 relative to shaft 270 exists. In the latter case, the threaded engagement of shaft 280 and plate 310 causes plate 310 to slide along arms 256. Pivoting element 258 is thus able to rotate about both the pivoting and axial directions.

It will be understood that changing or fluctuation of the rotational speed of one or both of shafts 270 and 280 can generate a reciprocating pivoting movement of pivoting element 258. For example, if the rotational speed of shaft 270 is held steady at a value V, and the rotational speed of shaft 280 fluctuates uniformly, steadily or step-wise from a value V+v to a value V−v, then the effect is a reciprocating pivoting motion. There is no pivoting when both rotational speeds are V, and that condition can correspond to pivoting member 258 and plate 310 being at extreme positions (e.g., with plate 310 abutting or close to a limit stop 331 or base 250 of mechanism 230). When the speed of shaft 280 is greater than V (i.e. between V and V+v or at V+v), then plate 310 moves in a one linear direction along arms 256 (either toward or away from base 250), and pivots member 258 in one angular direction (either clockwise or counterclockwise). When the speed of shaft 280 is less than V (i.e. between V and V−v or at V−v), then plate 310 moves in the other linear direction along arms 256, and pivots member 258 in the other angular direction.

With mechanism 230, it is possible to arrange pivoting of pivoting mechanism 258 from a first position that is substantially forward-looking (e.g. FIG. 8A), so that transducer 228 points along or substantially along a longitudinal axis of device 220, to a second position that is somewhat rearward-looking (e.g. FIG. 8C), so that transducer 228 points in a direction more than 90 degrees behind that forward-looking first position (i.e., past perpendicular to the longitudinal axis). Device 220 thus has the ability to look forward using ultrasound, as well as having a very wide angle and volume of available viewing through ultrasound transmission.

Figure 10:
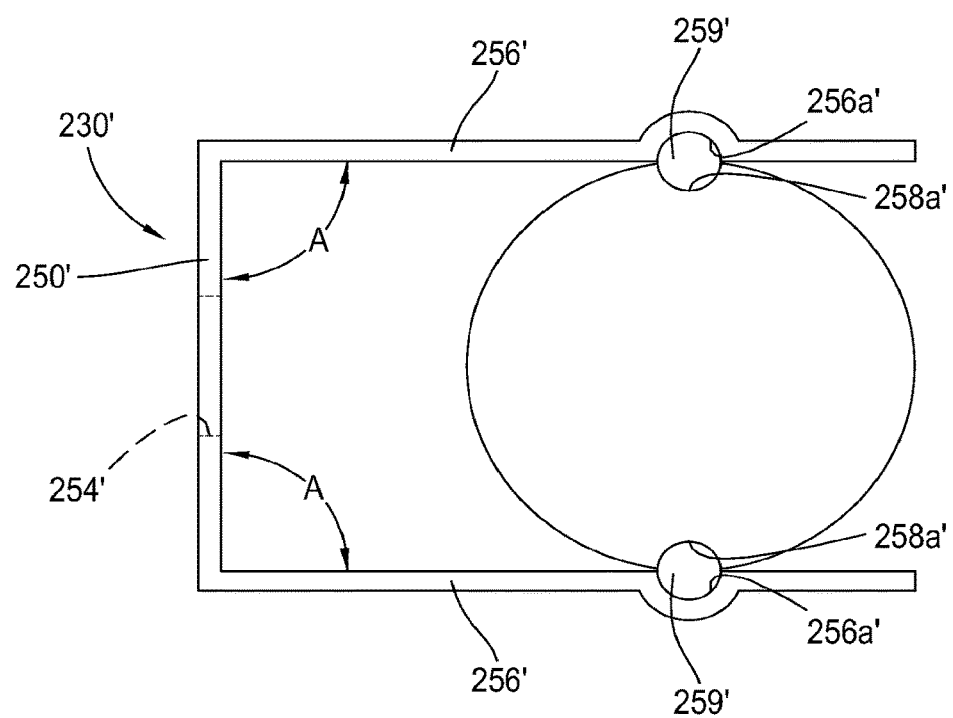
FIG. 10 is a top plan view of an alternative embodiment of a portion of the embodiment of FIG. 1 or 7.

FIG. 10 shows an alternative embodiment of a gimbal-type mechanism 230' that is similar in many respects to mechanism 230 described above, with similar parts indicated with the same number with an added prime. Mechanism 230' includes a base 250' that includes a hole 254' as described with respect to base 250, as well as arms 256'. In this embodiment, arms 256' are formed so that the angles A are less than 90 degrees prior to placing pivoting mechanism 258'. Arms 256' include a divot or indentation 256a' opposite each other, and pivoting mechanism 258' also include opposing divots or indentations 258a'. Indentations 256a' and 258a' are aligned when pivoting mechanism 258' is connected to mechanism 230', and are generally on the axis around which mechanism 258' pivots with respect to arms 256'. A respective insert 259' is placed in each indentation 256a', or between facing pairs of indentations 256a' and 258a'. Inserts 259' are spherical (e.g. a ball bearing) in the illustrated embodiment, to limit friction between them and the surfaces of arms 256' and pivoting mechanism 258' they separate, and may be of or coated with a low friction material such as Teflon. Other embodiments of one or both inserts 259 may have another shape that allows pivoting mechanism 258' to freely pivot within arms 256'. In a particular embodiment, one or both inserts 259' are made of or coated with a conductive material, and can therefore act as an electrical contact point between pivoting mechanism 258' (and/or the transducer connected or fixed to it) and the respective arm 256' (or a conductive surface of it) of mechanism 230'.

Pivoting mechanism 258' is sized so that when connected to arms 256' via inserts 259', arms 256' elastically deform outward, in the manner of flat springs. Angle A increases as arms 256' are deformed, and the elastic or spring force thus created in arms 256' is sufficient to keep pivoting mechanism 258' and inserts 259' in place. Pivoting of mechanism 258' (and a transducer connected or fixed to it) is around an axis joining inserts 259'.

As noted, transducer 228 may be substantially the same as embodiments described above with respect to transducer 28. In specific embodiments, transducer 228 is fixed to or forms part or all of pivoting mechanism 258. An exemplary transducer 228 (e.g. FIGS. 8A-8C) is a piezoelectric element 261 having a thin (compared to the piezoelectric material) conductive top electrode layer 263 and a thin conductive bottom electrode layer 265. An optional matching layer may be placed over top electrode layer 263, and an optional backing layer may be placed over bottom electrode layer 265. Layers 263, 265 are used as connection points to energize transducer 228 and/or send electrical signals from transducer 228, while the matching and/or backing layers (if present) can also be conductive and form an extension of the respective electrode layer. Further, layers 263 and 265 may be electrically connected, as by extending one layer around the side of piezoelectric element 261 to connect with the other layer, thus permitting both electrical connection points to be on one side of the assembly.

It will be understood that placing the externalized conductive layers 263, 265 can be accomplished using a selective plating or coating process with a conductive material such as gold. The process places a contact point on each side of piezoelectric element 261 from which electrical connections for transducer 228 can be made. As another example, bottom layer 265 may be made via an insert molded contact that passes through the wall of a molded polymer shell used to surround backing material. A top layer 263 can be made by welding, soldering or conductive-gluing to a small portion of the top surface of element 261. If present, a matching layer would be made with a small cut-out section to allow space for electrical connection to layer 263.

Electrical connections are made to the top surface of transducer 228 and to the bottom of transducer 228 (or the bottom of pivoting mechanism 258 electrically connected to transducer element(s)), for receiving and/or sending electrical impulses in the course of ultrasound scanning. In a particular embodiment, such electrical connections are connected to or from the pivot points for pivoting mechanism 258. In that case, the pivot points may be welded or soldered to flexible wire(s) (not shown) that run along mechanism 230 (e.g. along arms 256), which is electrically connected to a slip ring assembly (indicated schematically at 400) between mechanism 230 and application end motor 232. Such wires may be insulated and the welds or solder areas at the pivot points may be coated with an insulating material in the event a conductive fluid is present around mechanism 230, so as to prevent shorting of the electrical connections in the fluid.

Instead of such wire(s), one or both of arms 256 may be made of or coated at least in part with a conductive material, and the pivot points directly contact arms 256 or their conductive portions. Where arms 256 or a portion of them are used as conductors, base 250 is non-conductive, allowing arms 256 to be separately energized. As an example, the entire frame (base 250 and arms 256) may be made of a non-conductive material, and arms 256 coated at least partially with a conductive material. In another example, mechanism 230 is insert molded, with metal arms 256 extending from a non-conductive (e.g. polymer) base 250. In another example, base 250 and/or arms 256 may include at least two layers of conductive material separated by a non-conductive polymer (e.g. polyimide). In such examples in which both contacts or electrical lines are exposed, a non-conductive coupling fluid (e.g. silicon oil or other non-conductive oils) should be used. Where only one contact or electrical line is exposed, saline or other conductive fluid could be used as a coupling medium.

Figure 9:
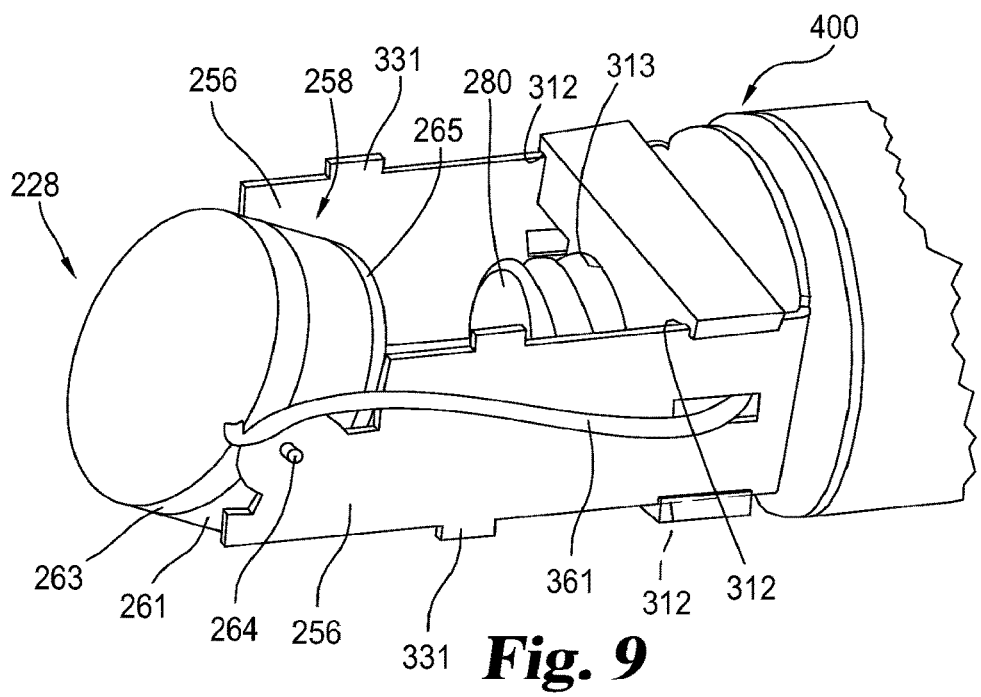
FIG. 9 is a perspective view of the embodiment of FIG. 7 with a particular electrical connection.

Other electrical connection examples use forcing member 360 as a conductor. For example, in an embodiment discussed above member 360 connects to pivoting member 258 (and/or to transducer 228) via tab T, and if made of or coated at least partially by a conductive material can thus act as a conductor from the bottom of transducer 228. The top surface of transducer 228 could be electrically connected as indicated above, e.g via one or both pivot points, wires, and/or arms 256. Particular embodiments may include an insulating layer on the outer surface of the forcing member 360, for example where a conductive coupling medium is used. If the forcing member 360 is not conductive or it is not desired to use it as a conductor, a wire 361 (FIG. 9) may be electrically connected to the bottom of transducer 228 and run alongside member 360 to a connection (e.g. a slip ring connection) at motor 232 or between motor 232 and mechanism 230. FIG. 9 shows a wire 361 connected at one end to a portion of pivoting member 258 and/or transducer 228, and extending through an opening in arm 256 to a connection (not shown) as previously indicated.

A slip ring assembly indicated schematically at 400 sits between base 250 and motor 232 in the illustrated embodiment. Slip ring embodiments are disclosed in U.S. Provisional Application No. 61/714,275 (filed Oct. 16, 2012) and International Application No. PCT/US2013/064611 (filed on the same date as the present application and entitled "Internal Transducer Assembly With Slip Ring"), each of which is incorporated herein by reference in its entirety. Rotating brushes of the slip ring structure are electrically connected to conductive layers or surfaces of arms 256, or to wiring or other conductors from transducer 228. The brushes contact a stationary ring on motor 232. The ring may be a flexible printed circuit board in a particular embodiment, which is electrically connected (e.g. by a wire or conductive layer on or in catheter 222 or a wall portion of catheter 222) past motor 234 to a conductor (e.g. a coaxial cable) extending to the device handle or other control. It will be understood that in other embodiments the brushes may be placed on motor 232 as stationary piece(s) and the ring may be placed on base 250 or other part of mechanism 230.

In the use of the terms "rotation" or "rotational," e.g. with respect to a rotational axis, it should be understood that even though rotation often implies an angle change much greater than 360°, the devices disclosed herein may be configured in certain embodiments so that the rotational angle may rotate through angles less than 360°. Similarly, in the use of the terms "pivot" or "pivoting," e.g. with respect to a pivoting axis, it should be understood that even though the term pivot often implies an angle change less than 360°, the devices disclosed herein may be configured in certain embodiments so that the pivoting angle may pivot through angles greater than 360°. In some instances the term "pivot" may be considered by some more natural than "rotate" or vice versa, but for the purposes of this application the terms "rotate" and "pivot" are used for clarity to indicate the axis about which a change in angle occurs, not the nature or magnitude of the angle change.

While the embodiments have been illustrated and described in detail in the drawings and foregoing description, the same is to be considered as illustrative and not restrictive in character, it being understood that only particular embodiments have been shown and described and that all changes and modifications that come within the spirit of the disclosure are desired to be protected. It will be understood that features or attributes noted with respect to one or more specific embodiments may be used or incorporated into other embodiments of the structures and methods disclosed.

What is claimed is:

1. An apparatus for ultrasound procedures, comprising: a transducer for emitting and/or receiving ultrasound signals; a first and a second motor, wherein the first motor is operatively connected to the transducer so that operation of the first motor turns the transducer around a longitudinal rotation axis, a pivoting mechanism operationally connected to the first motor so that the pivoting mechanism rotates in response to operation of the first motor, the pivoting mechanism having a base and pivoting member that is pivotable with respect to the base around a pivoting axis, the pivoting axis being substantially perpendicular to the longitudinal rotation axis, a forcing member operationally connected to the pivoting member, wherein a force applied via the forcing member controls pivoting of the pivoting member around the pivoting axis and wherein the second motor is operatively connected to the transducer so that pivoting motion of the transducer around the pivoting axis transverse to the longitudinal rotation axis is a function of the operation of the second motor, and wherein the pivoting mechanism includes a pair of arms extending from the base and a sliding plate adapted to slide along the arms and connected to the forcing member, the sliding plate being threadedly connected to the second shaft.

2. The apparatus of claim 1, wherein the first motor is a rotary motor and the second motor is one of a linear motor and a rotary motor.

3. The apparatus of claim 1, wherein the first motor turns a first shaft having a lumen and operatively connected to the transducer, and wherein the second motor operates a second shaft that extends through the lumen of the first shaft and is operatively connected to the transducer.

4. The apparatus of claim 1, wherein the transducer is at least part of the pivoting member.

5. The apparatus of claim 1, wherein the first motor turns a first shaft having a lumen and operatively connected to the transducer, and wherein the second motor operates a second shaft that extends through the lumen of the first shaft and is operatively connected to the transducer.

6. The apparatus of claim 5, wherein the second shaft is directly connected to the pivoting member.

7. The apparatus of claim 5, wherein the second shaft is connected to the pivoting member by a pivoting connector.

8. The apparatus of claim 1, wherein the forcing member is movable in two directions along the rotation axis by operation of the second motor, wherein movement of the forcing member in a first linear direction pivots the transducer in a first pivoting direction, and movement of the forcing member in a second linear direction pivots the transducer in an opposite second pivoting direction.

9. The apparatus of claim 1, wherein the first and second motors are separably operable at one or more speeds, whereby a desired ultrasound scan pattern can be obtained.

10. The apparatus of claim 1, wherein the first motor is configured so that the first motor turns faster when the pivoting mechanism is in a state such that the transducer is pointing in a direction relatively closer to the first motor's axis of rotation, and the first motor turns slower when the pivoting mechanism is in a state such that the transducer is pointing in a direction relatively farther from the first motor's axis of rotation.

11. The apparatus of claim 1, wherein the transducer is spring-biased to an initial orientation relative to the base, and when force applied via the forcing member is released, the pivoting member returns toward the initial orientation.

12. The apparatus of claim 1, wherein the pivoting mechanism is a gimbal mount apparatus.

13. The apparatus of claim 1, further comprising a tubular member for housing the transducer and the first and second motors, the tubular member having a distal chamber defined at least in part by a wall portion of the tubular member, the distal chamber housing at least the transducer and a medium, the wall portion and the medium having similar ultrasound passage characteristics to the part of the body into which the tubular member is inserted, so that reflection of ultrasound at the boundary of the medium and the wall portion and at the boundary of the wall portion and body environment is reduced to a level acceptable for imaging through the boundary.

14. The apparatus of claim 1, wherein the first and second motors are both rotary motors, and wherein pivoting motion of the transducer is a function of the difference between the rotational speeds of the first and second motors.

15. The apparatus of claim 1, wherein the forcing member is one of a flat bar and a formed wire.

16. The apparatus of claim 1, wherein the arms each include at least one limit stop for blocking movement of the sliding plate beyond the limit stops.

17. The apparatus of claim 1, wherein the pivoting mechanism has an unstressed condition in which the respective angles between each arm and the base are each less than 90 degrees, and wherein each of the arms has a respective indentation and at least one of the pivoting member and the transducer include opposing corresponding indentations, and further comprising a pair of inserts, each insert placed within respective corresponding indentations of the arms and pivoting member or transducer, so that the pivoting mechanism assumes a stressed condition in which the respective angles between each arm and the base is increased, creating spring force that is sufficient to keep the pivoting mechanism and inserts in place with respect to the arms.

18. An apparatus for ultrasound procedures, comprising: a transducer for emitting and/or receiving ultrasound signals; a first and a second motor, wherein the first motor is operatively connected to the transducer so that operation of the first motor turns the transducer around a longitudinal rotation axis, a pivoting mechanism operationally connected to the first motor so that the pivoting mechanism rotates in response to operation of the first motor, the pivoting mechanism having a base and pivoting member that is pivotable with respect to the base around a pivoting axis, the pivoting axis being substantially perpendicular to the longitudinal rotation axis, and a forcing member operationally connected to the pivoting member, wherein a force applied via the forcing member controls pivoting of the pivoting member around the pivoting axis, wherein the second motor is operatively connected to the transducer so that pivoting motion of the transducer around the pivoting axis transverse to the longitudinal rotation axis is a function of the operation of the second motor, wherein the first motor turns a first shaft having a lumen and operatively connected to the transducer, and wherein the second motor operates a second shaft that extends through the lumen of the first shaft and is operatively connected to the transducer, wherein the second motor is a linear motor, and wherein the forcing member comprises the second shaft, the second shaft extending substantially along the rotation axis, wherein operation of the second motor moves the second shaft along the rotation axis, the second shaft being operationally connected to the transducer to control the pivoting of the transducer around the pivoting axis.

19. The apparatus of claim 18, wherein the second shaft is directly connected to the pivoting member.

20. The apparatus of claim 18, wherein the second shaft is connected to the pivoting member by a pivoting connector.

21. The apparatus of claim 18, wherein the forcing member is movable in two directions along the rotation axis by operation of the second motor, wherein movement of the forcing member in a first linear direction pivots the transducer in a first pivoting direction, and movement of the forcing member in a second linear direction pivots the transducer in an opposite second pivoting direction.

22. The apparatus of claim 18, wherein the first and second motors are separably operable at one or more speeds, whereby a desired ultrasound scan pattern can be obtained.

23. The apparatus of claim 18, wherein the transducer is spring-biased to an initial orientation relative to the base, and when force applied via the forcing member is released, the pivoting member returns toward the initial orientation.

24. The apparatus of claim 18, wherein the pivoting mechanism is a gimbal mount apparatus.

25. The apparatus of claim 18, further comprising a tubular member for housing the transducer and the first and second motors, the tubular member having a distal chamber defined at least in part by a wall portion of the tubular member, the distal chamber housing at least the transducer and a medium, the wall portion and the medium having similar ultrasound passage characteristics to the part of the body into which the tubular member is inserted, so that reflection of ultrasound at the boundary of the medium and the wall portion and at the boundary of the wall portion and body environment is reduced to a level acceptable for imaging through the boundary.

26. The apparatus of claim 18, wherein the forcing member is one of a flat bar and a formed wire.

27. The apparatus of claim 18, wherein the arms each include at least one limit stop for blocking movement of the sliding plate beyond the limit stops.

28. The apparatus of claim 18, wherein the pivoting mechanism includes a pair of arms extending from the base, the pivoting mechanism having an unstressed condition in which the respective angles between each arm and the base are each less than 90 degrees, and wherein each of the arms has a respective indentation and at least one of the pivoting member and the transducer include opposing corresponding indentations, and further comprising a pair of inserts, each insert placed within respective corresponding indentations of the arms and pivoting member or transducer, so that the pivoting mechanism assumes a stressed condition in which the respective angles between each arm and the base is increased, creating spring force that is sufficient to keep the pivoting mechanism and inserts in place with respect to the arms.

29. An apparatus for ultrasound procedures, comprising: a transducer for emitting and/or receiving ultrasound signals; a first and a second motor, wherein the first motor is operatively connected to the transducer so that operation of the first motor turns the transducer around a longitudinal rotation axis, and a pivoting mechanism operationally connected to the first motor so that the pivoting mechanism rotates in response to operation of the first motor, the pivoting mechanism having a base and pivoting member that is pivotable with respect to the base around a pivoting axis, the pivoting axis being substantially perpendicular to the longitudinal rotation axis, wherein the second motor is operatively connected to the transducer so that pivoting motion of the transducer around the pivoting axis transverse to the longitudinal rotation axis is a function of the operation of the second motor, wherein the first motor is configured so that the first motor turns faster when the pivoting mechanism is in a state such that the transducer is pointing in a direction relatively closer to the first motor's axis of rotation, and the first motor turns slower when the pivoting mechanism is in a state such that the transducer is pointing in a direction relatively farther from the first motor's axis of rotation.

30. The apparatus of claim 29, wherein the first and second motors are both rotary motors, and wherein pivoting motion of the transducer is a function of the difference between the rotational speeds of the first and second motors.

31. The apparatus of claim 29, further comprising a forcing member operationally connected to the pivoting member, wherein a force applied via the forcing member controls pivoting of the pivoting member around the pivoting axis.

* * * * *